United States Patent [19]

Mosher et al.

[11] Patent Number: 5,063,224

[45] Date of Patent: Nov. 5, 1991

[54] R-CEFUROXIME AXETIL

[75] Inventors: Gerold L. Mosher; Michael V. Mullen, both of Indianapolis, Ind.

[73] Assignee: Eli Lilly and Company, Indianapolis, Ind.

[21] Appl. No.: 550,005

[22] Filed: Jul. 9, 1990

[51] Int. Cl.$^5$ ................. C07D 501/34; A61K 31/545
[52] U.S. Cl. ..................................... 514/202; 540/222
[58] Field of Search ................. 540/222, 221; 514/202

[56] References Cited

U.S. PATENT DOCUMENTS 4,602,012  7/1986  Weingarten .......................... 540/222
4,820,833  4/1989  Crisp et al. .......................... 540/220

FOREIGN PATENT DOCUMENTS 2145409A  3/1985  United Kingdom .

OTHER PUBLICATIONS

Sanderson, *Proceedings of a Symposium*, Jun. 12, 1987, Royal Society of Medicine Services Ltd., pp. 3–10.
Campbell, *Biochemical Pharmacology*, vol. 36, No. 14, pp. 2317–2324, 1987.

*Primary Examiner*—Nicholas S. Rizzo
*Attorney, Agent, or Firm*—Charles W. Ashbrook; Leroy Whitaker

[57] ABSTRACT

R-Cefuroxime axetil which is substantially free of the S-isomer is readily absorbed from the stomach and gastro-intestinal track of animals, and is therefore ideally suited to oral therapy of bacterial infections.

8 Claims, No Drawings

R-CEFUROXIME AXETIL

BACKGROUND OF THE INVENTION

This invention is directed to the preparation and use of the R-isomer of cefuroxime axetil in a form substantially free of the S-isomer.

Cefuroxime is a cephalosporin antibiotic having a broad spectrum of activity against both gram-positive and gram-negative microorganisms. The compound's use is limited to injectable administration because it is poorly absorbed from the gastro-intestinal tract following oral dosing. Crisp et al., in GB2,145,409A, describes the synthesis of the 1-acetoxyethyl ester of cefuroxime, now referred to as cefuroxime axetil. Cefuroxime axetil is a prodrug of cefuroxime which can be orally administered, thereby permitting more convenient and wider therapeutic use of cefuroxime. Unfortunately, cefuroxime axetil suffers from several deficiencies, including being rapidly hydrolyzed in the intestine, leaving substantial unabsorbable cefuroxime. Campbell et al., in *Biochemical Pharmacology*, Vol. 36, No. 14, pp 2317-2324, 1987, report the isolation and partial characterization of an esterase enzyme which is said to be responsible for converting cefuroxime axetil to cefuroxime in the gut. The ester portion of cefuroxime axetil, namely the 1-acetoxyethyl group, contains an asymmetric carbon atom at the 1-position, and accordingly cefuroxime axetil exists in the form of a mixture of the R- and S-isomers. Oral administration of the R,S-mixture of cefuroxime axetil results in only about fifty percent bioavailability of the cefuroxime antibiotic, due to low overall solutility and the rapid hydrolysis of the ester group by esterase enzymes located in the gut. The unabsorbable cefuroxime remaining in the gut lumen is suspected to be the cause of incomplete bioavailability, and the gastro-intestinal irritation generally observed.

We have now discovered that the individual S-isomer of cefuroxime axetil is hydrolyzed in animals much more rapidly than the R-isomer. Accordingly, an object of this invention is to provide R-cefuroxime axetil substantially free of the S-isomer, and to provide a method for administering R-cefuroxime axetil and not administering the S-isomer. Such selective administration results in surprisingly greater bioavailability of cefuroxime, and thus dramatically reduces the amount of unabsorbable cefuroxime remaining in the gut lumen, thereby diminishing adverse side effects attributable to cefuroxime.

SUMMARY OF THE INVENTION

This invention provides in substantially pure form R-cefuroxime axetil of the formula

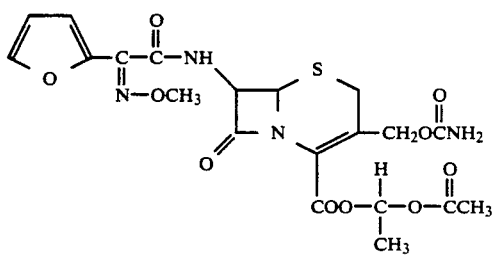

The invention further provides a pharmaceutical formulation comprising R-cefuroxime axetil substantially free of the S-isomer admixed with a conventional diluent or carrier therefor, and a method of treating bacterial infections comprising administering such substantially pure R-cefuroxime axetil. The invention additionally provides a method for preparing substantially pure R-cefuroxime axetil comprising selectively solubilizing such compound from a racemic mixture of R,S-cefuroxime axetil.

DETAILED DESCRIPTION OF THE INVENTION

According to one embodiment of this invention, there is provided R-cefuroxime axetil in substantially pure form. The term "substantially pure form" means R-cefuroxime axetil substantially free of S-cefuroxime axetil. A preferred compound is one in which such R-isomer is present in greater than about eighty-four percent, preferably about ninety percent or more, relative to the total R and S-cefuroxime axetil contained therein.

The substantially pure R-cefuroxime axetil of this invention is prepared by selectively solubilizing the R-isomer in a solvent in which the S-isomer is only minimally soluble relative to the R-isomer. Solvents commonly employed are those in which the R-isomer is about six times more soluble in a given volume than the S-isomer. The R-isomer is surprisingly more soluble than the S-isomer in organic solvents such as ketones, for example acetone and methyl ethyl ketone, nitriles such as acetonitrile, esters such as methyl acetate and ethyl acetate, alcohols such as methanol, ethanol, n-butanol and the like, and halogenated hydrocarbons such as dichloromethane, 1,2-dibromoethane, and chloroform. Generally, a mixture of R and S-cefuroxime axetil, prepared as described in GB 2,145,409A, and containing the R and S-isomers, is added to a solvent to form a slurry. The best results are obtained employing a solvent that provides sufficient solubility to maintain the desired volume at a minimum. Preferred solvents include alcohols such as methanol and ethanol. We have demonstrated that the R-isomer has a solubility in methanol of 391.4 mg/ml at 60° C., whereas the S-isomer has solubility of 89.97 mg/ml. In ethanol at 25° C., the R-isomer has a solubility of 12.0 mg/ml and the S-isomer is about 2.98 mg/ml. In isopropanol at 25° C., the R-isomer is 1.84 mg/ml, and the S-isomer is 0.44 mg/ml. In n-butanol at 25° C., the R-isomer is 1.0 mg/ml and the S-isomer is 0.3 mg/ml. In ethyl acetate at 25° C., the R-isomer is 13.42 mg/ml, and the S-isomer is 10.0 mg/ml.

The slurry mixture of RS-cefuroxime axetil in a solvent preferably is stirred or agitated at a temperature of about 24° C. to about 90° C. for a period of time from about one-half hour to about ten hours. Such conditions facilitate solution of the more soluble R-cefuroxime axetil, while permitting the undesired S-isomer to remain suspended in the solvent. The precise time of agitation and temperature are not critical, since all that is required is that a solubility equilibrium be established. Following the stirring or agitation, the mixture can be filtered by conventional techniques to remove the liquid phase. The liquid phase is recovered and can be concentrated by removal of the solvent under reduced pressure, thereby affording the substantially pure R-cefuroxime axetil as a dry powder, generally amorphous. The product can be readily crystallized by conventional methods utilizing common solvents such as alcohols and the like. The R-cefuroxime axetil of the invention can be crystallized directly from the liquid phase by conventional techniques, for instance by cooling the solution to a temperature of about 0° C. to about −100° C., or by adding a suitable antisolvent such as diethyl ether, hexane, cyclohexane or the like. Absence of water provides crystalline R-cefuroxime axetil as an anhydrate, whereas addition of water provides the crystalline R-cefuroxime axetil hemihydrate. Alternatively, the manner in which the R-cefuroxime axetil is exposed to water can determine the crystal form produced. For example, if water is added to an acetone solution of R-cefuroxime axetil, the anhydrous crystal form is produced, whereas if an acetone solution of R-cefuroxime axetil is added to water, the hemihydrate crystal form is produced.

As noted above, the surprisingly good solubility characteristics of R-cefuroxime axetil make it useful as an oral treatment for bacterial infections in animals. The R-isomer is readily absorbed in the stomach and intestine, well before the esterase enzymes located there are able to hydrolyze the axetil portion of the molecule. Accordingly, oral administration of R-cefuroxime axetil results in good absorption of antibiotic from the stomach and gut, resulting in drug levels of cefuroxime in the blood sufficient to effect rapid and effective control and irradiation of the bacterial infection throughout the animal system. Just as important, however, is the low incidence of hydrolysis in the intestine, and thus low concentration of cefuroxime as the free acid, which is essentially not absorbed from the gut, and the presence of which results in undesired intestinal irritations.

A further embodiment of this invention is therefore a method of treating bacterial infections comprising orally administering an antibacterially effective amount of R-cefuroxime axetil. The compound is active against a wide range of gram positive bacteria, including *Staphylococcus aureus*, *Streptococcus pyogenes*, and *Streptococcus pneumoniae*, as well as gram-negative bacteria such as *Haemophilus influenzae*, *Neisseria gonorrhoeae*, *Klebsiella pneumoniae*, and *Proteus mirabilis*. As such, R-cefuroxime axetil is useful in treating lower respiratory tract infections such as pneumonia, urinary tract infections, skin and skin structure infections, septicemia, gonorrhea, as well as bone and joint infections, caused for example by *S. aureus*. R-cefuroxime axetil will be administered at an adult dosage of about 500 mg. to about 2.0 g. every eight to ten hours until the infection is controlled or terminated. The compound is ideally suited to treatment of infants and children, typically at dosages of about 10 to about 200 mg/kg per day. The substantially pure R-cefuroxime axetil is well tolerated by infants and children due to its acceptable taste characteristics.

The substantially pure R-cefuroxime axetil of this invention can be formulated with any number of readily available pharmaceutical carriers and excipients for convenient oral administration. The compound will typically be formulated as a dry powder in a capsule, or molded into a tablet, or prepared as a syrup or suspension. Typical carriers and excipients which can be utilized include pharmaceutical carriers such as lactose, sorbitol, mannitol, starch, amylopectin, cellulose derivatives, calcium stearate, polyvinylpyrrolidone, and related pharmaceutical carriers and diluents. Suspensions and syrups can be formulated with water, glycerol, propylene glycol, vegetable oils, ethanol and similar liquid carriers. The formulations provided by this invention will contain from about 0.5 to about 95.0% by weight of the substantially pure R-cefuroxime axetil, admixed with the pharmaceutical carrier or diluent.

The practice of this invention is further illustrated by the following detailed examples, none of which are to be construed as limiting the invention in any respect.

EXAMPLE 1

Substantially pure R-cefuroxime axetil

One hundred grams of a mixture comprised of forty-nine percent (as determined by high performance liquid chromatography) S-cefuroxime axetil and fifty-one percent R-cefuroxime axetil were added to 338 ml of methanol at 24° C. The resulting slurry was heated to 60° C. and stirred for thirty minutes. The slurry was cooled to 24° C. and filtered. The solvent was removed from the filtrate to provide a powder identified by HPLC as 93% pure R-cefuroxime axetil, the remainder of which was S-cefuroxime axetil.

EXAMPLE 2

R-Cefuroxime Axetil - Production Scale

Three hundred sixty liters of methyl alcohol were added to a 200 gallon stainless steel reactor vessel. The reactor was purged with nitrogen gas, and heated to 50° C. To the warm methanol were added 173.2 kg of racemic cefuroxime axetil. The reaction suspension was heated at 60° C. and stirred for one hour. The reaction slurry was then cooled to 30° C. and filtered through a single plate stainless steel filter. The filter cake was dried by passing a stream of nitrogen over it for 15 minutes. Sixty liters of fresh methanol were added to the reactor, and then poured over the filter cake. All of the filtrate was collected together in a separate reactor. The filter cake was air dried at 40° C. to provide 102.2 kg of a white powder identified as S-cefuroxime axetil.

The filtrate that was collected from above (about 400 liters) was diluted by the addition of 120 liters of deionized water. The solution was cooled to 2° C., and then was stirred for 24 hours at that temperature. The solid crystals which had formed were collected by filtration. The reactor which held the filtrate was rinsed with 60 liters of fresh methanol, which was then washed through the filter cake. The filter cake was partially dried by passing a nitrogen stream over it for 15 minutes. The filter cake was then placed in a vacuum dryer in which it was dried at 40° C. for 6 days to provide 63.0 kg of crystalline anhydrous R-cefuroxime axetil. The product was analyzed and shown to contain 85% by weight of R-cefuroxime axetil and 15% by weight of S-cefuroxime axetil. Microbiological assay demonstrated the product had 99% biological potency.

EXAMPLE 3

To a round bottom flask containing 3.0 liters of methanol were added 789 g of racemic cefuroxime axetil. The mixture was a thick paste at 25° C. but became a slurry when heated to 50° C. for one hour and stirred. The slurry was cooled to 25° C. and stirring was continued at that temperature for 12 hours. The slurry was then filtered to provide a white powder that, when dried at 45° C. under reduced pressure, afforded 342 g of S-cefuroxime axetil. The filtrate from above was concentrated to about 600 ml by evaporation of solvent under reduced pressure. The solution was diluted by the addition of 600 ml of ethyl acetate, and then all solvents were removed by evaporation under reduced pressure to provide a dry powder identified as 362.5 g of crystalline R-cefuroxime axetil substantially free of S-isomer.

EXAMPLE 4

X-Ray Pattern of R-Cefuroxime Axetil

R-Cefuroxime axetil was prepared by the general procedures described above and recrystallized as follows. To 4.5 liters of acetone were added 150 g of substantially pure R-cefuroxime axetil. The solution was diluted by adding 15 liters of distilled water. The solution was stored at 5° C. for several days, and the crystalline product which had formed was collected by filtration and identified as anhydrous R-cefuroxime axetil.

The foregoing procedure was repeated, except the acetone solution of R-cefuroxime axetil was added to 15 liters of water. The crystalline product was collected and identified as R-cefuroxime axetil hemihydrate.

The two crystal forms of R-cefuroxime axetil were x-rayed utilizing a Nicolet I2V Diffractometer having a graphite monochromator and measured at a wavelength of 1.5418 Angstroms.

| Spacing, d (Angstroms) | Relative Intensities I/I max |
|---|---|
| X-Ray of R-Cefuroxime Axetil Anhydrate | |
| 24.73 | 0.15 |
| 11.01 | 1.00 |
| 9.79 | 0.19 |
| 9.56 | 0.04 |
| 7.78 | 0.19 |
| 7.33 | 0.03 |
| 6.93 | 0.18 |
| 6.81 | 0.03 |
| 6.14 | 0.07 |
| 5.49 | 0.10 |
| 4.87 | 0.21 |
| 4.67 | 0.03 |
| 4.56 | 0.33 |
| 4.46 | 0.14 |
| 4.38 | 0.08 |
| 4.32 | 0.01 |
| 4.21 | 0.10 |
| 4.16 | 0.08 |
| 4.07 | 0.04 |
| 3.89 | 0.14 |
| 3.82 | 0.05 |
| 3.70 | 0.14 |
| 3.64 | 0.05 |
| 3.54 | 0.12 |
| 3.45 | 0.03 |
| 3.31 | 0.16 |
| 3.18 | 0.02 |
| 3.04 | 0.05 |
| 2.96 | 0.01 |
| 2.77 | 0.04 |
| 2.63 | 0.02 |
| X-Ray of Cefuroxime Axetil Hemihydrate | |
| 12.21 | 0.10 |
| 11.69 | 0.23 |
| 10.71 | 0.38 |
| 9.65 | 0.44 |
| 8.52 | 0.40 |
| 8.14 | 0.05 |
| 7.44 | 0.51 |
| 7.03 | 0.32 |
| 6.88 | 0.37 |
| 6.55 | 0.09 |
| 6.32 | 0.17 |
| 6.10 | 0.16 |
| 5.58 | 0.68 |
| 5.43 | 0.35 |
| 5.35 | 0.15 |
| 5.01 | 0.09 |
| 4.85 | 0.61 |
| 4.70 | 0.37 |
| 4.65 | 0.20 |
| 4.51 | 0.17 |
| 4.33 | 0.43 |
| 4.20 | 1.00 |
| 4.06 | 0.22 |
| 3.94 | 0.38 |
| 3.91 | 0.40 |
| 3.84 | 0.29 |
| 3.77 | 0.27 |
| 3.58 | 0.32 |
| 3.51 | 0.37 |
| 3.40 | 0.14 |
| 3.35 | 0.19 |
| 3.32 | 0.15 |
| 3.26 | 0.08 |
| 3.16 | 0.11 |
| 3.08 | 0.06 |
| 2.97 | 0.12 |
| 2.89 | 0.09 |
| 2.81 | 0.10 |
| 2.77 | 0.10 |
| 2.71 | 0.06 |
| 2.68 | 0.11 |

EXAMPLE 5

The following study was conducted to establish that S-cefuroxime axetil is hydrolyzed to cefuroxime acid much more rapidly by esterase enzymes in blood serum than the R-cefuroxime axetil of this invention.

Blood serum was obtained from an 11.5 kg male dog two days prior to sacrifice. The whole blood was centrifuged for fifteen minutes at 3500 rpm and 4° C. The serum thus collected was diluted with ten parts Sorenson's phosphate buffer pH 7.4.

A solution was prepared by dissolving 0.29 mg of R-cefuroxime axetil in 50 ml of Sorenson's phosphate buffer pH 7.4. Another solution was prepared by dissolving 0.26 mg of S-cefuroxime acetil in 50 ml of Sorenson's phosphate buffer pH 7.4.

Triplicate test tubes containing 2.75 ml of the R-cefuroxime axetil solution, and triplicate tubes containing 2.75 ml of the S-cefuroxime axetil solution, were each heated to 37° C. and diluted with 0.25 ml of the serum preparation from above. Aliquot portions (200 µl each) from each tube were drawn at thirty minute intervals, diluted with 100 µl of 10% aqueous trichloracetic acid, and 100 µl of acetonitrile. The samples were centrifuged at 3000 rpm for five minutes to precipitate the proteins, and then transferred to autosampler tubes for determination of cefuroxime free acid content. Analysis was conducted using a Beckman 344 gradient high performance liquid chromatography column packed with zorbox $C_{18}$ reverse phase, with an eluant comprised of 40 parts methanol and 60 parts water. Standard integration of HPLC curves were carried out to convert the area to a mg/ml equivalent.

Results of the triplicate study are as follows:

| Time of Analysis (After Mixing Drug With Serum) | mg/ml of R-Cefuroxime Axetil | mg/ml. of S-Cefuroxime Axetil |
|---|---|---|
| 0 Min. | $6.357 \times 10^{-3}$ | $3.16 \times 10^{-3}$ |
| 30 | $5.99 \times 10^{-3}$ | $1.62 \times 10^{-3}$ |
| 60 | $4.13 \times 10^{-3}$ | $0.98 \times 10^{-3}$ |
| 90 | $3.47 \times 10^{-3}$ | $0.607 \times 10^{-3}$ |
| 120 | $2.97 \times 10^{-3}$ | $0.427 \times 10^{-3}$ |
| 0 | $6.35 \times 10^{-3}$ | $3.23 \times 10^{-3}$ |
| 30 | $4.67 \times 10^{-3}$ | $1.54 \times 10^{-3}$ |
| 60 | $3.98 \times 10^{-3}$ | $0.968 \times 10^{-3}$ |

| Time of Analysis (After Mixing Drug With Serum) | mg/ml of R-Cefuroxime Axetil | mg/ml. of S-Cefuroxime Axetil |
| --- | --- | --- |
| 90  | $3.38 \times 10^{-3}$ | $0.687 \times 10^{-3}$ |
| 120 | $2.91 \times 10^{-3}$ | $0.373 \times 10^{-3}$ |
| 0   | $6.58 \times 10^{-3}$ | $3.16 \times 10^{-3}$ |
| 30  | $4.82 \times 10^{-3}$ | $1.57 \times 10^{-3}$ |
| 60  | $4.02 \times 10^{-3}$ | $0.955 \times 10^{-3}$ |
| 90  | $3.58 \times 10^{-3}$ | $0.626 \times 10^{-3}$ |
| 120 | $2.69 \times 10^{-3}$ | $0.375 \times 10^{-3}$ |

The results of the above experiment establish that S-cefuroxime axetil is hydrolyzed much more rapidly in blood serum than the R-cefuroxime axetil of this invention. Accordingly, the compound of this invention has a longer half-life.

EXAMPLE 6

The following experiment establishes that S-cefuroxime axetil is hydrolyzed much more rapidly in the dog gut than is the R-cefuroxime axetil of this invention.

About 18 inches of intestine was removed from a 13 month old male dog weighing 11.5 kg. The intestine section was washed several times with Sorenson's solution, and then sliced open lengthwise. The intestine cells were collected by scraping the inner surface of the intestine with a glass microscope slide, and provided 6.10 g of cell tissue. The cell tissue was placed in 30.5 ml of Sorenson's pH 7.5 phosphate buffer. The mixture was homogenized for 30 seconds with a Tek-Mar tissuemizer. The resulting suspension was centrifuged at 4° C. at 3500 rpm for 15 minutes.

Following the general procedure of Example 2, 0.277 mg of R-cefuroxime axetil was dissolved in 50 ml of Sorenson's pH 7.4 buffer, and 0.263 mg of S-cefuroxime axetil was dissolved in 50 ml of Sorenson's pH 7.4 buffer.

Triplicate tubes of 2.75 ml of the R-cefuroxime axetil solution, and triplicate tubes of the S-cefuroxime axetil solution, were allowed to equilibrate to 37° C., and then 0.25 ml of the intestine mixture from above was added to each tube. Aliquot samples were withdrawn every 30 minutes for two hours, and each 200 μl of 10% aqueous trichloroacetic acid and 100 μl of acetonitrile. The samples were stirred for five minutes at 3000 rpm, and then decanted to an autosampler for assay, utilizing a standard Bio-Rad protein assay. The assays were analyzed for unchanged R- or S-cefuroxime axetil and afforded the following results.

| Time of Analysis (After Mixing Drug With Gut Cells) | mg/ml of R-Cefuroxime Axetil | mg/ml. of S-Cefuroxime Axetil |
| --- | --- | --- |
| 0 Min. | $5.531 \times 10^{-3}$ | $1.829 \times 10^{-3}$ |
| 30  | $2.531 \times 10^{-3}$ | $4.035 \times 10^{-4}$ |
| 60  | $1.743 \times 10^{-3}$ | $1.697 \times 10^{-4}$ |
| 90  | $5.585 \times 10^{-4}$ | $6.088 \times 10^{-5}$ |
| 120 | $1.287 \times 10^{-4}$ | |
| 0   | $5.531 \times 10^{-3}$ | $1.797 \times 10^{-3}$ |
| 30  | $2.404 \times 10^{-3}$ | $2.413 \times 10^{-4}$ |
| 60  | $1.605 \times 10^{-3}$ | $1.924 \times 10^{-4}$ |
| 90  | $5.888 \times 10^{-4}$ | $8.988 \times 10^{-5}$ |
| 120 | $1.452 \times 10^{-4}$ | $6.590 \times 10^{-6}$ |
| 0   | $5.476 \times 10^{-3}$ | $1.810 \times 10^{-3}$ |
| 30  | $2.638 \times 10^{-3}$ | $1.797 \times 10^{-4}$ |
| 60  | $1.599 \times 10^{-3}$ | $1.435 \times 10^{-4}$ |
| 90  | $7.679 \times 10^{-4}$ | $9.848 \times 10^{-5}$ |
| 120 | $2.361 \times 10^{-4}$ | $1.092 \times 10^{-5}$ |

Experiments similar to those of Examples 2 and 3 were conducted and form the basis for our conclusion that S-cefuroxime axetil is hydrolyzed about 25 fold faster than R-cefuroxime axetil in bood serum, and about 3 fold faster in intestinal preparations.

EXAMPLE 7

| Formulation of Pediatric Oral Suspension | |
| --- | --- |
| Ingredient | Amount |
| Substantially pure R-cefuroxime axetil | 2.5 grams |
| Sorbitol solution (70% N.F.) | 40 ml |
| Saccharin | 20 mg |
| Cherry flavor | 50 mg |
| Distilled water q.s. | 100 ml |

The sorbitol solution is added to 20 ml of distilled water and the R-cefuroxime axetil is suspended therein. The saccharine and flavoring are added and dissolved. The volume is adjusted to 100 ml with distilled water. Each ml of syrup contains 25 mg of R-cefuroxime axetil. This oral formulation is ideally suited for pediatric use.

EXAMPLE 8

| Preparation of 1.0 g capsule | |
| --- | --- |
| Ingredient | Amount |
| Substantially pure R-cefuroxime axetil | 1.0 grams |
| Lactose | 200 mg |
| Corn Starch | 100 mg |
| | 1.3 g |

The ingredients are blended to uniformity and encapsulated into gelatin capsules. Such capsules are orally administered to adult humans at the rate of about two each day for the treatment of upper respiratory bacterial infections, including pharyngitis and tonsillitis.

We claim:

1. Substantially pure R-cefuroxime axetil.
2. A mixture of claim 1 in which the R isomer is present at greater than about 90% relative to the S-isomer.
3. A process for preparing substantially pure R-cefuroxime axetil comprising adding an amount of a mixture of R and S-cefuroxime axetil to an amount of solvent in which the S-isomer is much less soluble than the R-isomer, said amount of solvent being that which approximates the minimum amount which will dissolve the R-isomer, stirring the mixture until solubility equilibrium is reached, separating the liquid and solid phases, and removing the solvent from the liquid phase containing substantially pure R-cefuroxime axetil.
4. The process of claim 3 wherein the solvent is methanol.
5. A method of treating bacterial infections in humans comprising orally administering an antibacterially effective amount of the compound of claim 1.
6. A pharmaceutical formulation comprising the compound of claim 1 admixed with a pharmaceutically acceptable carrier therefor.
7. Crystalline R-cefuroxime axetil anhydrate substantially free of S-cefuroxime axetil and having the following x-ray pattern:

| Spacing, d (Angstroms) | Relative Intensities I/I max |
| --- | --- |
| 24.73 | 0.15 |

-continued

| Spacing, d (Angstroms) | Relative Intensities I/I max |
|---|---|
| 11.01 | 1.00 |
| 9.79 | 0.19 |
| 9.56 | 0.04 |
| 7.78 | 0.19 |
| 7.33 | 0.03 |
| 6.93 | 0.18 |
| 6.81 | 0.03 |
| 6.14 | 0.07 |
| 5.49 | 0.10 |
| 4.87 | 0.21 |
| 4.67 | 0.03 |
| 4.56 | 0.33 |
| 4.46 | 0.14 |
| 4.38 | 0.08 |
| 4.32 | 0.01 |
| 4.21 | 0.10 |
| 4.16 | 0.08 |
| 4.07 | 0.04 |
| 3.89 | 0.14 |
| 3.82 | 0.05 |
| 3.70 | 0.14 |
| 3.64 | 0.05 |
| 3.54 | 0.12 |
| 3.45 | 0.03 |
| 3.31 | 0.16 |
| 3.18 | 0.02 |
| 3.04 | 0.05 |
| 2.96 | 0.01 |
| 2.77 | 0.04 |
| 2.63 | 0.02 |

8. Crystalline R-cefuroxime axetil hemihydrate substantially free of S-cefuroxime axetil and having the following x-ray pattern:

| Spacing, d (Angstroms) | Relative Intensities I/I max |
|---|---|
| 12.21 | 0.10 |
| 11.69 | 0.23 |
| 10.71 | 0.38 |
| 9.65 | 0.44 |
| 8.52 | 0.40 |
| 8.14 | 0.05 |
| 7.44 | 0.51 |
| 7.03 | 0.32 |
| 6.88 | 0.37 |
| 6.55 | 0.09 |
| 6.32 | 0.17 |
| 6.10 | 0.16 |
| 5.58 | 0.68 |
| 5.43 | 0.35 |
| 5.35 | 0.15 |
| 5.01 | 0.09 |
| 4.85 | 0.61 |
| 4.70 | 0.37 |
| 4.65 | 0.20 |
| 4.51 | 0.17 |
| 4.33 | 0.43 |
| 4.20 | 1.00 |
| 4.06 | 0.22 |
| 3.94 | 0.38 |
| 3.91 | 0.40 |
| 3.84 | 0.29 |
| 3.77 | 0.27 |
| 3.58 | 0.32 |
| 3.51 | 0.37 |
| 3.40 | 0.14 |
| 3.35 | 0.19 |
| 3.32 | 0.15 |
| 3.26 | 0.08 |
| 3.16 | 0.11 |
| 3.08 | 0.06 |
| 2.97 | 0.12 |
| 2.89 | 0.09 |
| 2.81 | 0.10 |
| 2.77 | 0.10 |
| 2.71 | 0.06 |
| 2.68 | 0.11 |

* * * * *